United States Patent
Burger et al.

(10) Patent No.: US 6,452,957 B1
(45) Date of Patent: Sep. 17, 2002

(54) SINTERED SHAPED BODY REINFORCED WITH PLATELETS

(75) Inventors: Wolfgang Burger, Plochingen; Gundula Kiefer, Wernau; Eduardo Bellido, Ebersbach; Hans Andersch, Heiningen, all of (DE)

(73) Assignee: Ceramtec AG Innovative Ceramic Engineering, Plochingen (DE)

( * ) Notice: Subject to any disclaimer, the term of this patent is extended or adjusted under 35 U.S.C. 154(b) by 0 days.

(21) Appl. No.: 09/509,839

(22) PCT Filed: Nov. 2, 1998

(86) PCT No.: PCT/EP98/06914

§ 371 (c)(1),
(2), (4) Date: Jul. 6, 2000

(87) PCT Pub. No.: WO99/23048

PCT Pub. Date: May 14, 1999

(30) Foreign Application Priority Data

Oct. 31, 1997 (DE) .......................... 197 48 232

(51) Int. Cl.⁷ ............................. F27D 1/00; B24D 3/02; C04B 35/48
(52) U.S. Cl. ......................... 373/137; 51/309; 501/105
(58) Field of Search ................. 373/137, 155, 373/164; 501/104, 105, 127, 87; 65/305; 51/309; 264/86

(56) References Cited

U.S. PATENT DOCUMENTS

| | | | |
|---|---|---|---|
| 4,316,964 A | 2/1982 | Lange | 501/105 |
| 4,770,673 A | 9/1988 | Ketcham et al. | 51/309 |
| 4,792,538 A | 12/1988 | Pavlica et al. | 501/127 |
| 4,823,359 A | 4/1989 | Ault et al. | 373/137 |
| 4,889,548 A | 12/1989 | Kriegesmann et al. | 65/305 |
| 5,002,911 A * | 3/1991 | Matsumoto et al. | 501/105 |
| 5,106,788 A | 4/1992 | Suzuki et al. | 501/87 |
| 5,667,548 A | 9/1997 | Graule | 264/86 |
| 5,830,816 A | 11/1998 | Burger et al. | 501/105 |

FOREIGN PATENT DOCUMENTS

| | | |
|---|---|---|
| EP | 0 282 879 | 9/1988 |
| EP | 0 259 400 | 9/1990 |
| EP | 0 199 459 | 1/1992 |
| EP | 0 236 507 | 1/1992 |
| EP | 0 214 291 | 4/1992 |
| EP | 0 542 815 | 8/1994 |
| WO | 85/01936 | 5/1985 |
| WO | WO 90/11980 | 10/1990 |
| WO | WO 92/02470 | 2/1992 |
| WO | WO 94 02429 | 2/1994 |
| WO | 94/24064 | 10/1994 |

OTHER PUBLICATIONS

W. Burger, "Umwandlungs–und plateletverstaerkte Aluminiumoxidmatrixwertstoff (Teil 1)" Keramische Zeitschrift, vol. 49, No. 12, Dec. 1997, pp. 1067–1070.

W. Burger, Umwandlungs–und plateletverstaerkte Aluminiumoxidmatrixwerkstoffe (Teil 2) Keramische Zeitschrift, vol. 50, No. 1, Jan. 1999, pp. 18–22.

* cited by examiner

Primary Examiner—Tu Ba Hoang
(74) Attorney, Agent, or Firm—Foley & Lardner

(57) ABSTRACT

The invention relates to a sintered shaped body comprising a matrix material that contains an aluminum oxide/chromium oxide mixed crystal and an additional mixed crystal selected from at least one mixed crystal according to one of the general formulas $La_{0.9}Al_{11.76-x}Cr_xO_{19}$, $Me^1Al_{11-x}Cr_xO_{17}$, $Me^2Al_{12-x}Cr_xO_{19}$, $Me^{2'}Al_{12-x}Cr_xO_{19}$ and/or $Me^3Al_{11-x}Cr_xO_{18}$, wherein $Me^1$ stands for an alkali metal, $Me^2$ represents an alkaline earth metal, $Me^{2'}$ stands for cadmium, lead or mercury and $Me^3$ represents a rare earth metal and x has a value ranging from 0.0007 to 0.045.

20 Claims, No Drawings

SINTERED SHAPED BODY REINFORCED WITH PLATELETS

BACKGROUND OF THE INVENTION

1. Field of the Invention

The subject-matter of the present invention is a sintered shaped body consisting of a matrix material that contains an aluminium oxide/chromium oxide mixed crystal and which is in situ reinforced with platelets.

2. Description of Related Art

The use of an oxide ceramic material for pressing-tools for shaping components of glass or ceramic material containing glass is specified in DE-A-36 08 854. In addition to cubic and tetragonal zirconium dioxide, aluminium oxide, chromium oxide, spinel and an Al-Cr-mixed oxide ($AlCr_2O_3$) that is not defined with regard to its quantitative composition are also specified as matrix materials. The individual proposals for the matrix components enjoy equality in this connection so there is not offered any teaching for the selection of a particular matrix component or for the proportion of the quantity of, for example, zirconium dioxide to be incorporated in the matrix. Stabilizing oxides, such as, for example, yttrium oxide ($Y_2O_3$) in a quantity of 3.5 to 12, preferably 8 to 10, or magnesium oxide (MgO) in a quantity of 6.0 to 16, preferably 8 to 14 mol %, and cerium oxide ($CeO_2$) in a quantity of 3.5 to 12 mol %, preferably 8 to 10 mol %, relative can also be present in addition to the components mentioned above. A size between 5 and 5000 nm, corresponding to 0.005 to 5 $\mu$m, is mentioned as the particle size for the particles incorporated in a polycrystalline matrix.

A further proposal for a so-called "conversion-reinforced" ceramic composition, in which a finely distributed solid solution of $ZrO_2$—$HfO_2$ in a solid solution of either aluminium oxide, containing chromium oxide, or mullite, containing chromium oxide, is specified, is found in WO 85/01936 and in that case is put forward for high-temperature fields of application, such as, for example, for diesel engines and gas turbines. The proportion of chromium oxide considered between 3 and 30 mol %, in particular a proportion of 20 mol % chromium oxide, cooperating with a proportion of 10 to 20 mol % hafnium dioxide, is to be used to improve the hardness and to set a low level of thermal conductivity. Rising proportions of chromium oxide and hafnium dioxide result in a decrease in the thermal conductivity. Noticeable increases in hardness are first found when there are comparatively high concentrations of chromium oxide—approximately 20 mol %, relative to 20 mol % $HfO_2$. An order of magnitude of 5 $\mu$m is specified for the grain size of the incorporated $ZrO_2$—$HfO_2$ phase in the examples of this specification, and the fact that tetragonal modification is not obtained is attributed to the fact that there not been achieved any success in obtaining the dispersed $ZrO_2$—$HfO_2$ solid solution with the sufficient degree of fineness. No addition of stabilizing oxides is mentioned in this specification. The fracture-toughness values attained lie in the range between 5 and approximately 6.5 MPavm.

EP-A-199 459 relates to ceramic compositions with high levels of toughness and provides for the cooperation of zirconium dioxide, partly stabilized zirconium dioxide, solid solutions of zirconium dioxide/hafnium dioxide, solid solutions of partly stabilized zirconium dioxide/hafnium dioxide, partly stabilized hafnium dioxide and hafnium dioxide with mixtures of metal oxides, in particular yttrium niobium oxide ($YNbO_4$) or yttrium tantalum oxide ($YTaO_4$), with the yttrium ion of the mixed oxides even being replaced in part by a cation of a rare earth metal, for example $La^{+3}$, $Ce^{+4}$, $Ce^{+3}$, $Pr^{+2}$, $Tm^{+3}$. According to a further variant of this specification, the ceramic alloy that is described, that is, for example $ZrO_2$, can be mixed, whilst adding $YNbO_4$ in a quantity of at least 5 % by volume, with, for example, $\alpha$-aluminium oxide or even $Al_2O_3$—$Cr_2O_3$, mullite or titanium carbide. The disadvantage of this known composition can be seen in the fact that, as a consequence of the mixed oxides containing Nb or Ta that are produced, a further grain-boundary develops with the ceramic products and a softening point sets in that is not yet at a sufficiently high level for many fields of application.

Similarly, U.S. Pat. No. 4,770,673 describes a ceramic cutting tool, 20 to 45% of which consists of a zirconium dioxide alloy, containing 1 to 4 mol % of a mixed metal oxide, and 55 to 80% by weight of which consists of a hard ceramic composition, with the mixed metal oxides consisting of the group of $YNbO_4$, $YTaO_4$, $MNbO_4$, $MTaO_4$ and mixtures thereof, and M consisting of a cation, which is provided for the substitution of the yttrium cation, and being selected from $Mg^{+2}$, $Ca^{+2}$, $Sc^{+3}$ and rare earth metal ions, consisting of the group $LA^{+3}$, $Ce^{+4}$, $Ce^{+3}$, $Pr^{+3}$, $Nd^{+3}$, $Sm^{+3}$, $Eu^{+3}$, $Gd^{+3}$, $Tb^{+3}$, $Dy^{+3}$, $HO^{+3}$, $Er^{+3}$, $Tm^{+3}$, $Yb^{+3}$ and $Lu^{+3}$ and mixtures thereof. In addition to aluminium oxide and, for example, sialon, SiC, $Si_3N_4$, as a hard ceramic material $Al_2O_3$—$Cr_2O_3$ also comes into consideration, in which a proportion of $Cr_2O_3$ of up to approximately 5 mol % is provided. Here again, as previously, there is the disadvantage that too low a softening range results in the ceramic material on account of the alloying constituents that are added to the $ZrO_2$ in the form of the mixed oxides which contain niobium or tantalum.

U.S. Pat. No. 4,316,964 relates to a composition that is also taken into consideration for the production of cutting plates and which consists of 95–5% by volume aluminium oxide and 5–95% by volume zirconium dioxide with the addition of approximately 0.5–5.5 mol % yttrium oxide, 0.5 to 10 mol % cerium oxide, 0.4 to 4 mol % erbium oxide and 0.5 to 5 mol % lanthanum oxide, relative to zirconium dioxide.

A sintered shaped body that is also provided for use as a cutting plate in accordance with EP-A-282 879 consists of a matrix containing whiskers and, moreover, particles of, for example, silicon carbide, silicon nitride, sialon, aluminium oxide and zirconium dioxide. The whiskers can be made of the same materials as the particles. Zirconium dioxide is mentioned here as the matrix material in addition to mullite and aluminium oxide. Moreover, the sintered shaped body can also contain the usual sintering aids, such as, for example, the oxides of magnesium, chromium or yttrium. Of the rare earth oxides that are suitable those which are preferred are the oxides of lanthanum, samarium, gadolinium, dysprosium, holmium, erbium, thulium, ytterbium and lutetium. Fracture-toughness values of more than 10 $MPam^{1/2}$ are specified.

A ceramic material with very high levels of toughness and wear-resistance for use as a metal-removing cutting tool is known from DE-A-35 29 265. The composition provides, in addition to 20 to 50% by weight titanium carbide and 18 to 79.9% by weight aluminium oxide, 0.1 to 2% by weight of a sintering aid which is selected from the group: MgO, CaO, $SiO_2$, $ZrO_2$, NiO, $Th_2O_3$, AlN, TiO, $TiO_2$, $Cr_2O_3$ and/or at least one oxide of the rare earths. $Y_2O_3$, $Dy_2O_3$, $Er_2O_3$, $Ho_2O_3$, $Gd_2O_3$ and/or $Tb_4O_7$ are mentioned as rare earth oxides. The sintering aids are used to prevent the grain growth in the case of the aluminium oxide and enter into combination with the latter, promoting the sintering process of the ceramic material.

A sintered body containing 40 to 99 mol % partly stabilized zirconium dioxide and 1 to 60 mol % aluminium oxide and, furthermore, as sintering aids, small quantities of the oxides of Mn, Fe, Co, Ni, Cu and Zn for the acceleration of the sintering process, is known from EP-A-214 291. The oxides of yttrium, magnesium, calcium or cerium are proposed for the purpose of setting a tetragonal phase proportion of 65 % or more. 1.3 to 4 mol % is mentioned as the quantity of yttrium oxide that is to be added and which can be replaced completely or partly by the other stabilizing oxides in a quantity of 0.01 to 12 mol %.

A zirconium dioxide having more than a 65% tetragonal phase and being contained in a high-density ceramic body, 60 to 99 mol % of which consists of aluminium oxide, is specified in EP-A-236 507. Less than 3 mol % $Y_2O_3$, less than 12 mol % MgO or CaO and less than 14 mol % $CeO_2$, relative to the ceramic composition, are proposed for the stabilization of the zirconium oxide. In order to improve the sintering capacity and in order to suppress the grain growth and thus to attain a particularly high density, the material also contains transition metal oxides of Mn, Fe, Co, Ni, Cu and Zn, which can be added as such or as hydroxides, nitrates, chlorides inter alia to the starting composition. The disadvantage of this known material is that the maximum hardness of 1,750 $kg/mm^2$ is not yet sufficient for many fields of application, in particular in the case of cutting tools for machining.

The addition of chromium oxide to aluminium oxide, where at least 10% by weight chromium oxide is used, has been proposed for the production of a refractory material in U.S. Pat. No. 4,823,359. Alternatively, a mixture consisting of aluminium oxide/zirconium dioxide can also be used instead of the aluminium oxide. The comparatively high porosity that is desired for refractory articles and a low level of fracture toughness can be inferred from the permitted size of the grains, up to 50 μm, before sintering. The use of stabilizing oxides and the presence of the zirconium dioxide, possibly used in a specific modification thereof, are not mentioned. In addition, chromium oxide together with aluminium oxide and zirconium dioxide is used in accordance with U.S. Pat. No. 4,792,538 to produce refractory articles. The quantity of chromium oxide here is 5 to 25% by weight, with preferably 16% by weight being used. The porosity here lies in the range of approximately 14 to 15%; the addition of stabilizing oxides and the presence of zirconium dioxide in a specific modification thereof are not addressed.

WO 90/11980 relates to a ceramic material in which platelet-like grains of strontium aluminate in a molar ratio of $SrO/Al_2O_3$ between 0.02 and 0.2 are incorporated in a matrix of $ZrO_2$, $Al_2O_3$ or a mixture of $Al_2O_3$ and $ZrO_2$, consisting predominantly of $ZrO_2$, (platelet-reinforcement in situ). The hardness values that are attained are comparatively low even in the case of comparatively high proportions of aluminium oxide.

The in situ platelet-reinforcement of oxidic materials with chromium oxide doped $SrAl_{12}O_{19}$ platelets is also described in EP 0 542 815.

SUMMARY OF THE INVENTION

The underlying object of the present invention has consisted in improving the known materials and making sintered shaped bodies available that have a high level of strength and in which good fracture toughness is combined with a simultaneously high level of hardness. The present invention provides a sintered shaped body which meets these requirements and which, in consequence of its spectrum of properties, has a comparatively high level of wear resistance. The sintered shaped body in accordance with the invention is suitable for use as a cutting tool, in particular as a cutting plate, especially as a cutting plate for machining cast and steel materials. The properties of the sintered shaped body in accordance with the invention also render possible its use in particular as a cutting plate for interrupted cutting. Furthermore, the sintered shaped body in accordance with the invention can be used in other tribological applications.

DETAILED DESCRIPTION OF PREFERRED EMBODIMENTS

Surprisingly, it has been found that platelets corresponding in terms of structure can be produced, not just, as described in the prior art, for example in EP-A-0 542 815, with strontium oxide, but also with other specific oxides. The precondition for the platelet formation is the development of a hexagonal crystal structure of the platelets which are to be formed in situ. If the material system $Al_2O_3$—$Cr_2O_3$—$ZrO_2$—$Y_2O_3$ ($Ce_2O_3$) is used as the matrix, it is possible with a great variety of oxides to form the following platelets in situ. On alloying of alkali metal oxides, the corresponding alkali metal $Al_{11-x}Cr_xO_{17}$-platelets are formed, on alloying of alkaline earth metal oxides, the corresponding alkaline earth metal $Al_{12-x}Cr_xO_{19}$-platelets are formed, on alloying of CdO, PbO, HgO, the corresponding (Cd, Pb or $HgAl_{12-x}Cr_xO_{19}$)-platelets are formed and on alloying of rare earth metal oxides the corresponding rare earth metal $Al_{11-x}Cr_xO_{18}$-platelets are formed. Moreover, $La_2O_3$ can form the compound $La_{0.9}Al_{11.76-x}Cr_xO_{19}$. Platelets are also formed if the matrix contains no $Cr_2O_3$. The platelets then formed correspond to the general formulae: alkali metal $Al_{11}O_{17}$, alkaline earth metal $Al_{12}O_{19}$, (Cd, Pb or $HgAl_{12}O_{19}$) or rare earth metal $Al_{12}O_{18}$.

The solution to the problem of achieving the object in accordance with the invention provides a sintered shaped body which, as a constituent has a quite specific composition. In addition to the conversion reinforcement which is attained as a result of the incorporation of a zirconium dioxide which contains stabilizing oxides, in a ceramic matrix, the invention provides that the matrix contains a mixed crystal of aluminium oxide/chromium oxide. Furthermore, the invention provides that the zirconium dioxide, incorporated in the matrix, and the chromium oxide, forming the mixed crystal together with the aluminium oxide, are in a specific molar ratio with respect to each other. This measure makes it possible for particular hardness values to be attained even in the case of comparatively high proportions of zirconium dioxide that may be required in order to obtain a particularly good level of fracture toughness. On the other hand, in the case of low proportions of zirconium dioxide there may even be a comparatively small chromium-oxide content, inhibiting embrittlement of the material.

One or more of the oxides of cerium, praseodymium and terbium and/or yttrium oxide can be used as stabilizing means for the zirconium oxide. 10 to 15 mol % of the oxides of cerium, praseodymium and terbium and/or 0.2 to 3.5 mol % yttrium oxide, relative to the mixture of zirconium dioxide and stabilizing oxides, are preferably used.

The quantity of stabilizing oxides that is added is then selected so that the zirconium dioxide is present predominantly in the tetragonally modified form, and the proportion that is cubically modified, relative to zirconium dioxide, is 0 to 5 % by volume.

The indication that the zirconium dioxide containing the stabilizing oxides, and chromium oxide, should be in a specific molar ratio produces specific relationships for the other components, since, for example, with a falling proportion of zirconium dioxide, the proportions of stabilizing oxides, relative to the sintered shaped body, also decrease, whilst, on the other hand, the proportion of aluminium oxide rises. Relative to the aluminium oxide of the sintered shaped body, the chromium oxide present therein has a weight of 0.004 to 6.57 % by weight, with the chromium oxide and the zirconium dioxide, containing the stabilizing oxides, being in the specifiedmolar ratio.

In accordance with the invention, the matrix material contains an aluminium oxide/chromium oxide mixed crystal and a further mixed crystal in accordance with one of the general formulae $Me^1Al_{11-x}Cr_xO_{17}$, $Me^2Al_{12-x}Cr_xO_{19}$, $Me^{2'}Al_{12-x}Cr_xO_{19}$ or $Me^3Al_{11-x}Cr_xO_{18}$, where $Me^1$ stands for an alkali metal, $Me^2$ stands for an alkaline earth metal, $Me^{2'}$ stands for cadmium, lead or mercury, and $Me^3$ stands for a rare earth metal. $La_{0.9}Al_{11.76-x}Cr_xO_{19}$ can also be added as a mixed crystal to the matrix material, in which case x can then assume values of 0.0007 to 0.045.

In accordance with the invention, as one embodiment, a sintered shaped body is provided that has a matrix material which is characterised in that a1) 60 to 98% by volume of the matrix material a2) contains 67.1 to 99.2% by volume of an aluminium oxide/chromium oxide mixed crystal and a3) 0.8 to 32.9% by volume of a further mixed crystal, which is selected from at least one mixed crystal in accordance with one of the general formulae $La_{0.9}Al_{11.76-x}Cr_xO_{19}$, $Me^1Al_{11-x}Cr_xO_{17}$, $Me^2Al_{12-x}Cr_xO_{19}$, $Me^{2'}Al_{12-x}Cr_xO_{19}$ and/or $Me^3Al_{11-x}Cr_xO_{18}$, where $Me^1$ stands for an alkali metal, $Me^2$ stands for an alkaline earth metal, $Me^{2'}$ stands for cadmium, lead or mercury, and $Me^3$ stands for a rare earth metal, and x corresponds to a value of 0.0007 to 0.045, and b) the matrix material contains 2 to 40% by volume stabilized zirconium dioxide.

One effect that increases the toughness results from the zirconium dioxide that is incorporated in the mixed-crystal matrix, whilst the chromium addition counteracts any drop in the hardness values when the proportion of zirconium dioxide rises. The mixed crystal of the above-mentioned formulae that is additionally formed by the addition of the above-mentioned metal oxides gives rise to the effect that, even at higher temperatures, it imparts to the sintered shaped body a further improved level of toughness. The wear resistance of these sintered shaped bodies under the influence of raised temperatures is therefore also improved.

According to a further embodiment, the wear resistance of the sintered shaped bodies can be further improved as a result of the incorporation in the matrix material of 2 to 25% by volume of one or more of carbides, nitrides or carbonitrides of the metals of the 4th and 5th subgroups of the periodic system of elements—relative to the matrix material. The proportion of these hard materials is preferably 6 to 15% by volume. Titanium nitride, titanium carbide and titanium carbonitride are particularly suitable.

According to a particularly preferred further embodiment of the invention, the molar ratio of the zirconium dioxide, containing the stabilizing oxides, to chromium oxide is adjusted as a function of the proportion of zirconium dioxide present in the sintered shaped body in such a way that, with low proportions of zirconium dioxide, there are also small quantities of chromium oxide present therein. What has proved to be especially expedient in this connection is an adjustment of the molar ratio of zirconium dioxide: chromium oxide so that it lies in the following ranges:

2–5% by volume zirconium dioxide 1,000:1 to 100:1>5–15% by volume zirconium dioxide 200:1 to 40:1>15–30% by volume zirconium dioxide 100:1 to 20:1>30–40% by volume zirconium dioxide 40:1 to 20:1.

In order to obtain the zirconium dioxide so that it is predominantly in the tetragonally modified form, it is recommended in accordance with the invention that the adjusted grain size of the zirconium dioxide does not exceed 2 μm. Apart from the possible proportions of zirconium dioxide that are in a cubically modified form in a quantity of up to 5% by volume, in addition small quantities of the monoclinic form of modification can also be present, although these should also not exceed a maximum quantity of 10% by volume and preferably are less than a quantity of 5% by volume, a quantity of even less than 2% by volume being especially preferred.

In a preferred embodiment, the sintered shaped body in accordance with the invention contains, in addition to the specified components, impurities that have been dragged in, merely still in an unavoidable manner, and which, in accordance with a further preferred embodiment of the invention, amount to no more than 0.5% by volume. In a particularly preferred embodiment, the sintered shaped body merely consists of the aluminium oxide-chromium oxide mixed crystal and one of the mixed crystals of the formulae $Me^1Al_{11-x}Cr_xO_{17}$, $Me^2Al_{12-x}Cr_xO19$, $Me^{2'}Al_{12-x}Cr_xO_{19}$ or $Me^3Al_{11-x}Cr_xO_{18}$ and also of the zirconium dioxide that contains the stabilizing oxides and is incorporated in the matrix consisting of the mixed crystals which have been mentioned. Further phases, such as, for example, grain-boundary phases, which are formed when aluminium oxide and magnesium oxide are used together, or further crystalline phases, as develop in the case of the additions of substances known from the prior art, such as $YNbO_4$ or $YTaO_4$ and which have an insufficiently high softening point, are not present in this particularly preferred embodiment of the sintered shaped body in accordance with the invention. The oxides of Mn, Cu, Fe that are known from the prior art and which likewise result in the development of further phases, also give rise to a reduced softening point and result in low edge-strength levels. The use of these materials is therefore precluded in the case of this particularly preferred embodiment.

The zirconium dioxide is preferably present in a quantity of not more than 30% by volume, but also not in a quantity of less than 15% by volume. If between 15 and 30% by volume zirconium dioxide is present, the molar ratio between the zirconium dioxide, containing the stabilizing oxides, and chromium oxide lies, in a way that is especially preferred, between 40:1 and 25:1.

According to a further preferred embodiment, the proportion of zirconium dioxide present in a tetragonally modified form is not more than 95% by volume. The observance of a grain size of the incorporated zirconium dioxide in the range of 0.2 to 1.5 μm is especially preferred. On the other hand, an average grain size of the aluminium oxide/chromium oxide mixed crystal in the range of 0.6 to 1.5 μm has proved to be particularly suitable. In addition, if carbides, nitrides and carbonitrides of the metals of the 4th and 5th subgroup of the PSE are also used, these are used with a grain size of 0.5 to 3 μm. The grains of the mixed crystals of the formulae $Me^1Al_{11-x}Cr_xO_{17}$, $Me^2Al_{12-x}Cr_xO_{19}$, $Me^{2'}Al_{12-x}Cr_xO_{19}$ or $Me^3Al_{11-x}Cr_xO_{18}$ have a length/thickness ratio in the range of 5:1 to 15:1. Their maximum length in this connection amounts to 12 μm, their maximum thickness being 1.5 μm.

The Vickers hardness of the sintered shaped bodies in accordance with the invention is greater than 1,750 [$HV_{0.5}$], yet preferably is not more than 1,800 [$HV_{0.5}$].

The microstructure of the sintered shaped bodies in accordance with the invention is free of microcracks and has a degree of porosity of not more than 1.0%. The sintered shaped body can also contain whiskers, although not of silicon carbide.

The sintered shaped body preferably does not contain any of the substances that are widely used as grain-growth inhibitors, such as, for example, magnesium oxide.

The in situ platelet-reinforcement provided in accordance with the invention also occurs when the matrix contains no $Cr_2O_3$. This is provided in accordance with the invention if a drop in the hardness values does not constitute a disturbing effect. The platelets that are formed without $Cr_2O_3$ then correspond to the general formulae $Me^1Al_{11}O_{17}$, $Me^2Al_{12}O_{19}$, $Me^{2'}Al_{12}O_{19}$ or $Me^3Al_{11}O_{18}$. Even with these sintered shaped bodies, the same preferred embodiments can in principle be made available as they can be made available with the sintered shaped bodies that contain $Cr_2O_3$ in the matrix material. Furthermore, in this respect, the statements made above for the sintered shaped bodies with $Cr_2O_3$ in the matrix material apply in an analogous manner to the sintered shaped bodies without $Cr_2O_3$ in the matrix material.

During sintering, the stabilizing oxides are dissolved in the $ZrO_2$-lattice and stabilize the latter's tetragonal modification. For the purpose of producing the sintered shaped bodies and in order to attain a structure which is free of further undesirable phases, preferably raw materials are used that are of a high level of purity, that is, aluminium oxide and zirconium dioxide with a purity of more than 99%. The degree of impurities is preferably even substantially less. In particular, $SiO_2$-proportions of more than 0.5% by volume, relative to the finished sintered shaped body, are undesirable. The unavoidable presence of hafnium oxide in a small quantity of up to 2% by weight within the zirconium dioxide is excluded from this regulation.

The production of the sintered shaped body in accordance with the invention is effected by sintering pressure or by hot-pressing a mixture of aluminium oxide/zirconium dioxide/chromium oxide and stabilizing oxides or a mixture of these components, to which in addition an alkali metal oxide, an alkaline earth metal oxide, CdO, PbO, HgO, a rare earth metal oxide or $La_2O_3$ and/or one or more nitrides, carbides and carbonitrides of the 4th and 5th subgroup of the periodic system of elements (PSE) are added. Examples of mixes are specified in Table 1. The addition of yttrium oxide and chromium oxide can also be effected in the form of yttrium chromium oxide ($YCrO_3$), whilst the alkali metal, alkaline metal earth, cadmium, lead, mercury, rare earth metal oxides or the lanthanum oxide can preferably be added in the form of their salts, in particular as carbonates. However, even the addition of ternary compounds, which are decomposed and rearranged during sintering, is possible. Various ceramic mixtures have been produced by grinding and mixing. A temporary binding agent was added to the ground mixtures and the mixtures subsequently spray-dried. Green bodies were pressed out from the spray-dried mixtures, and these green bodies were sintered under standard conditions.

An alternative way to produce the green bodies is directly from the suspension. For this purpose, the mixture with a solids content of over 50% by volume in an aqueous suspension is ground. The pH-value of the mixture is then to be set at 4–4.5. After grinding, urea and a quantity of the enzyme urease, which is suitable for breaking down the urea, are added before this suspension is poured off into a mould. As a result of the enzyme-catalyzed urea—decomposition, the pH-value of the suspension is shifted to 9, in which case the suspension coagulates. The green body thus produced is dried and sintered after removal from the mould. The sintering process can be effected without pressure, although even pre-sintering, followed by subsequent high-temperature isostatic redensification, is possible. Further details regarding this method (DCC-method) are disclosed in WO 94/02429 and in WO 94/24064, to which express reference is made.

The term sintering without pressure herein covers both sintering under atmospheric conditions and also sintering in a protective gas or under vacuum. The shaped body is preferably first pre-sintered without pressure to 90 to 95% theoretical density and subsequently redensified by means of high-temperature isostatic pressing or gas-pressure sintering. The theoretical density can be increased, as a result, to a value of more than 99.5%.

A series of factors can attain substantial significance during the production of the ceramic materials based on the multi-component systems that have been mentioned. In particular, during the treatment of the powder mixtures, the dispersion and grinding can have particular influence upon the properties of the ceramic material in accordance with the invention. In this connection, the grinding method and the grinding unit itself can have an effect upon the result. Even the solids content of the grinding suspension used can also contribute to the dispersion.

The influencing parameters and their effect upon the mechanical properties are presented in greater detail in the following examples. The following combination of solids was used for the individual tests:

| | |
|---|---|
| $Al_2O_3$ | 73.11% by weight |
| $ZrO_2$ | 23.57% by weight |
| $La_2O_3$ | 2.48% by weight |
| $YCrO_3$ | 0.84% by weight |

A 60% by weight slip was used for tests V1–V4. In test V5, the solids content was reduced to 55% by weight. A vibration mill was used in order to carry out test V1. Tests V2 and V3 were carried out on a laboratory attrition mill; in V2 grinding was carried out for 1 hour, with the duration of grinding in V3 being 2 hours. In test V4 a quantity of 30 kg was treated in a continuous attrition mill. Test V5 was carried out in the laboratory attrition mill for a grinding period of 2 hours.

The results of the strength-analyses for the individual tests are presented in the following:

| | 4-point flexural strength | | | | |
|---|---|---|---|---|---|
| | Mean value [MPa] | Min | Max | Stand. dev. +/− | Weibull m |
| V1 | 692 | 480 | 835 | 105 | 7 |
| V2 | 789 | 297 | 942 | 162 | 4 |
| V3 | 1033 | 695 | 1243 | 113 | 10 |
| V4 | 1214 | 930 | 1373 | 93 | 15 |
| V5 | 997 | 781 | 1156 | 96 | 13 |

Preferred fields of application of the sintered shaped bodies in accordance with the invention lie in their use as cutting tools for cutting paper, textile material and foils, although use as a cutting plate for machining cast iron or steel materials, in particular for interrupted cutting, is particularly preferred. What is to be understood by this is that many small smooth cuts can be made on the work piece successively over time, in which case the cutting plate is heated greatly during the engagement with the work piece that is to be machined and before the engagement that follows is cooled briefly so that alternating thermal stress of the cutting plate results. The use of the sintered shaped bodies in accordance with the invention as artificial prostheses in medical engineering represents a particularly preferred field of application.

TABLE 1

|  | Example 1 [% by weight] | Example 2 [% by weight] | Example 3 [% by weight] | Example 4 [% by weight] | Example 5 [% by weight] | Example 6 [% by weight] |
| --- | --- | --- | --- | --- | --- | --- |
| $Al_2O_3$ | 73.30 | 58.62 | 73.60 | 84.16 | 66.95 | 63.53 |
| $Cr_2O_3$ | 0.86 | 1.20 | 0.40 | 0.10 | 0.86 | 0.76 |
| Oxide | 1.09* | 0.22** | 1.06* | 5.63*** | 0.95* | 1.06**** |
| $ZrO_2$ | 23.47 | 38.16 | 23.14 | 8.5 | 23.64 | 29.09 |
| $Y_2O_3$ | 1.28 | 1.80 | 0.13 |  | 1.30 |  |
| $CeO_2$ |  |  | 1.67 | 1.61 |  | 5.54 |
| TiN |  |  |  |  | 6.3 |  |

*$La_2O_3$;
**$Er_2O_3$;
***BaO;
****$Dy_2O_3$

What is claimed is:

1. Sintered shaped body having a matrix material, comprising
   a1) 60 to 98% by volume of the matrix material
   a2) contains 67.1 to 99.2% by volume of an aluminum oxide/chromium oxide mixed crystal and
   a3) 0.8 to 32.9% by volume of a further mixed crystal, which is selected from at least one mixed crystal in accordance with one of the general formulae $La_{0.9}Al_{11.76-x}Cr_xO_{19}$, $Me^1Al_{11-x}Cr_xO_{17}$, $Me^2Al_{12-x}Cr_xO_{19}$, $Me^{2'}Al_{12-x}Cr_xO_{19}$ and $Me^3Al_{11-x}Cr_xO_{18}$, where $Me^1$ stands for an alkali metal, $Me^2$ stands for an alkaline earth metal excluding strontium, $Me^{2'}$ stands for cadmium, lead or mercury, and $Me^3$ stands for a rare earth metal, and x corresponds to a value of 0.0007 to 0.045, and
   b) the matrix material contains 2 to 40% by volume tetragonally stabilized zirconium dioxide.

2. Sintered shaped body according to claim 1, wherein 2 to 15 mol % of one or more stabilizing oxides of cerium, praseodymium and terbium and 0.2 to 3.5 mol % yttrium oxide, relative to the mixture of zirconium dioxide and stabilizing oxides are employed as stabilizing means for the zirconium oxide, with the quantity of stabilizing oxides, that is added being selected so that the zirconium dioxide is present predominantly in the tetragonally modified form, and the proportion that is cubically modified, relative to zirconium dioxide, is 0 to 5% by volume.

3. Sintered shaped body according to claim 2, wherein the molar ratio between the zirconium dioxide, containing the stabilizing oxides, and chromium oxide amounts to 1,000:1 to 20:1, and the zirconium dioxide has a grain size that does not exceed 2 μm.

4. Sintered shaped body consisting of a matrix material, comprising
   a1) 60 to 98% by volume of the matrix material consists of
   a2) 67.1 to 99.2% by volume of an aluminum oxide/chromium oxide mixed crystal and
   a3) to 0.8 to 32.9% by volume of a mixed crystal, which is selected from a mixed crystal in accordance with one of the general formulae $La_{0.9}Al_{11.76-x}Cr_xO_{19}$, $Me^1Al^{11-x}Cr_xO_{17}$, $Me^2Al_{12-x}Cr_xO_{19}$ or $Me^3Al_{11-x}Cr_xO_{18}$ where $Me^1$ stands for an alkali metal, $Me^2$ stands for an alkaline earth metal, $Me^{2'}$ stands for cadmium, lead or mercury, and $Me^3$ stands for a rare earth metal excluding strontium, with x corresponding to a value of 0.0007 to 0.045,
   b) with there being incorporated in the matrix material 2 to 40% by volume zirconium dioxide, which
   c) contains as stabilizing oxides more than 2 to 15 mol % of one or more of the oxides of cerium, praseodymium and terbium and/or 0.2 to 3.5 mol % yttrium oxide, relative to the mixture of zirconium-dioxide and stabilizing oxides, with
   d) the quantity of stabilizing oxides that is added being selected so that the zirconium dioxide is present predominantly in the tetragonally modified form, and the proportion that is cubically modified, relative to zirconium dioxide being 0 to 5% by volume,
   e) the molar ratio between the zirconium dioxide, containing the stabilizing oxides, and chromium oxide amounting to 1,000:1 to 20:1,
   f) proportions of components complementing each other to give 100% by volume of the sintered shaped body, and
   g) the zirconium dioxide having a grain size that does not exceed 2 μm.

5. Sintered shaped body according to claim 1, wherein the matrix material also contains, in addition, 2 to 25% by volume of one or more of the carbides, nitrides and carbonitrides of the metals of the fourth and fifth subgroups of the periodic table of the elements—relative to the matrix material.

6. Sintered shaped body according to claim 1, wherein the molar ratio of the zirconium dioxide, containing the stabilizing oxides, to chromium oxide lies in the following ranges:
   2–5% by volume zirconium dioxide 1,000:1 to 100:1>5–15% by volume zirconium dioxide 200:1 to 40:1>5–30% by volume zirconium dioxide 100:1 to 20:1>30–40% by volume zirconium dioxide 40:1 to 20:1.

7. Sintered shaped body according to claim 1, wherein no more than 30% by volume zirconium dioxide is contained therein.

8. Sintered shaped body according to claim 1, wherein the zirconium dioxide is modified tetragonally to at least 90% by volume.

9. Sintered shaped body according to claim 1, wherein the average grain size of the aluminum oxide/chromium oxide mixed crystal amounts to 0.6 to 1.5 $\mu$m.

10. Sintered shaped body according to claim 1, wherein the grain size of the zirconium dioxide lies between 0.2 and 1.5 $\mu$m.

11. Sintered shaped body according to claim 1, wherein no more than 0.5% by volume unavoidable impurities, relative to the sintered shaped body, are contained therein.

12. Sintered shaped body according to claim 1, wherein the Vickers hardness·[$Hv_{0.5}$] is >1,800.

13. Method for producing a sintered shaped body in accordance to claim 1, wherein a mixture, which contains aluminum oxide, zirconium dioxide, chromium oxide, tetragonal zirconium oxide, stabilizing oxides and at least one oxide from the group of alkali metal oxides, alkaline earth metal oxides, CdO, PbO, HgO, rare earth metal oxides and/or $La_2O_3$, is ground, a temporary binding agent is added to the ground mixture, this mixture is spray-dried, green bodies are pressed out from this mixture, and the latter are sintered under standard conditions.

14. Method for producing a sintered shaped body in accordance with claim 13, wherein the green body is pre-sintered without pressure to a density of 50 to 95% and subsequently subjected to high-temperature isostatic redensification.

15. Method for producing a sintered shaped body in accordance with claim 1, wherein a mixture which contains aluminum oxide, chromium oxide, tetragonal zirconium oxide, if applicable stabilizing oxides and at least one oxides, Cdo, PbO, HgO rare earth oxides and/or $La_2O_3$, n an aqueous suspension with a solids content of more than 50% by volume is ground whilst observing a pH-value of a 4 to 4.5, is subsequently mixed with urea and urcase, is poured off into a mould and after subsequent coagulation is removed from the mould and sintered or pre-sintered and subjected to high-temperature isostatic subjected to high-temperature isostatic redensification.

16. A cutting tool for cutting paper, textile material and foils, comprising a sintered shaped body according to claim 1.

17. A cutting plate for machining cast iron or steel materials, comprising a sintered shaped body according to claim 1.

18. A cutting plate for interrupted cutting of cast iron and steel materials, comprising a sintered shaped body according to claim 1.

19. A component for artificial prostheses in medical engineering, comprising a sintered shaped body according to claim 1.

20. Sintered shaped body having a matrix material, wherein the matrix material contains at least one of the platelets in accordance with one of the general formulae $Me^1Al_{11}O_{17}$, $Me^2Al_{12}O_{19}$, $Me^2Al_{12}O_{19}$ where $Me^1$ stands for an alkali cadmium, lead or mercury, and $Me^3$ stands for a rare earth metal, and the matrix material contains tetragonally stabilized zirconium dioxide.

* * * * *